United States Patent
Yan et al.

(10) Patent No.: US 12,029,747 B2
(45) Date of Patent: Jul. 9, 2024

(54) USE OF BAICALIN IN PREPARATION OF DRUG FOR TREATING TUMOR IRRESPONSIVE TO IMMUNE CHECKPOINT INHIBITORS (ICIS)/UNDERGOING HYPERPROGRESSION

(71) Applicant: BEIJING FRIENDSHIP HOSPITAL, CAPITAL MEDICAL UNIVERSITY, Beijing (CN)

(72) Inventors: Dan Yan, Beijing (CN); Yu Zhang, Beijing (CN); Wei Zhao, Beijing (CN); Bangwei Cao, Beijing (CN); Aiting Wang, Beijing (CN); Jianglan Long, Beijing (CN)

(73) Assignee: BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 18/373,980

(22) Filed: Sep. 28, 2023

(65) Prior Publication Data
US 2024/0180943 A1    Jun. 6, 2024

Related U.S. Application Data

(63) Continuation of application No. PCT/CN2023/099383, filed on Jun. 9, 2023.

(30) Foreign Application Priority Data

Dec. 2, 2022 (CN) .......................... 202211537380.3

(51) Int. Cl.
| A61K 31/7048 | (2006.01) |
| A61K 45/06 | (2006.01) |
| A61P 35/00 | (2006.01) |

(52) U.S. Cl.
CPC .......... *A61K 31/7048* (2013.01); *A61K 45/06* (2013.01); *A61P 35/00* (2018.01)

(58) Field of Classification Search
None
See application file for complete search history.

(56) References Cited

U.S. PATENT DOCUMENTS

| 2019/0192602 A1 | 6/2019 | Cheng et al. |
| 2020/0368273 A1* | 11/2020 | Wada ..................... A61K 45/06 |

FOREIGN PATENT DOCUMENTS

| CN | 111000860 A | 4/2020 | |
| CN | 114642732 A | 6/2022 | |
| CN | 114870009 A | 8/2022 | |
| CN | 115624562 A | 1/2023 | |
| WO | WO-2022134433 A1 * | 6/2022 | ............. A61K 45/06 |

OTHER PUBLICATIONS

Ke, M., Zhang, Z., Xu, B., Zhao, S., Ding, Y., Wu, X., . . . & Dong, J. (2019). Baicalein and baicalin promote antitumor immunity by suppressing PD-L1 expression in hepatocellular carcinoma cells. International immunopharmacology, 75, 105824. (Year: 2019).*
Cheng, Y., Li, H., Zhang, L., Liu, J. J., Yang, C. L., & Zhang, S. (2021). Current and future drug combination strategies based on programmed death-1/programmed death-ligand 1 inhibitors in non-small cell lung cancer. Chinese Medical Journal, 134(15), 1780-1788. (Year: 2021).*
Kang, D. H., Chung, C., Sun, P., Lee, D. H., Lee, S. I., Park, D., . . . & Lee, J. E. (2022). Circulating regulatory T cells predict efficacy and atypical responses in lung cancer patients treated with PD-1/PD-L1 inhibitors. Cancer Immunology, Immunotherapy, 1-10. (Year: 2022).*
Takahiro Kamada, et al., PD-1+ regulatory T cells amplified by PD-1 blockade promote hyperprogression of cancer, PNAS, 2019, pp. 9999-10008, vol. 116, No. 20.
Mengyun Ke, et al., Baicalein and baicalin promote antitumor immunity by suppressing PD-L1 expression in hepatocellular carcinoma cells, International Immunopharmacology, 2019, pp. 1-10, vol. 75, 105824.
Salem Billan, et al., Treatment after progression in the era of immunotherapy, Lancet Oncol, 2020, pp. e463-e476, vol. 21.

* cited by examiner

*Primary Examiner* — Dale R Miller
(74) *Attorney, Agent, or Firm* — Bayramoglu Law Offices LLC

(57) ABSTRACT

A use of baicalin in preparation of a drug for treating a tumor irresponsive to immune checkpoint inhibitors (ICIs)/undergoing hyperprogression is provided, where the non-response to ICIs/hyperprogression of the tumor is caused by excessive Foxp3$^+$Treg cells; the targeted tumor is one selected from the group consisting of melanoma, non-small cell lung cancer (NSCLC), renal cell carcinoma (RCC), liver cancer, colorectal cancer (CRC), urothelial bladder cancer, and pancreatic cancer; and the ICIs is one or a mixture of two or more selected from the group consisting of a PD-1 inhibitor, a PD-L1 inhibitor, and a CTLA-4 inhibitor. In the present disclosure, baicalin is used in combination with ICIs to inhibit a number of Foxp3$^+$Treg cells in a tumor to play an anti-tumor sensitization effect, which can effectively treat a variety of tumors irresponsive to ICIs/undergoing hyperprogression caused by excessive Foxp3$^+$Treg cells.

2 Claims, 5 Drawing Sheets

USE OF BAICALIN IN PREPARATION OF DRUG FOR TREATING TUMOR IRRESPONSIVE TO IMMUNE CHECKPOINT INHIBITORS (ICIS)/UNDERGOING HYPERPROGRESSION

CROSS REFERENCE TO THE RELATED APPLICATIONS

This application is a continuation application of International Application No. PCT/CN2023/099383, filed on Jun. 9, 2023, which is based upon and claims priority to Chinese Patent Application No. 202211537380.3, filed on Dec. 2, 2022, the entire contents of which are incorporated herein by reference.

TECHNICAL FIELD

The present disclosure belongs to the field of biomedicine, and in particular relates to a use of baicalin in preparation of an anti-tumor drug used in combination with immune checkpoint inhibitors (ICIs). Specifically, the present disclosure provides a use of baicalin in preparation of a drug for treating a tumor irresponsive to ICIs/undergoing hyperprogression.

BACKGROUND

ICIs are first-line or second-line therapeutic plans for most tumor patients clinically. However, it has been clinically observed that more than 80% of tumor patients cannot respond to ICIs, and another 15% of tumor patients undergo hyperprogression, which is called hyperprogressive disease (HPD). In clinical treatment, if the above two situations occur, traditionally, a measure such as changing the therapeutic plan is usually taken to avoid further tumor progression (The Lancet Oncology, 21(10), e463-α476). The re-selection of a therapeutic plan may make the optimal treatment time window missed and may also bring physical, mental, financial, and material stresses to the patient. How to restore an immune response of a patient without changing the original therapeutic plan when the patient does not respond to ICIs or undergoes hyperprogression is the key for solving the above problems and is also the most feasible research direction for clinical treatment.

Studies have shown that non-responsiveness to ICIs or HPD is associated with highly-proliferative Foxp3$^+$Treg cells in the tumor (Proceedings of the National Academy of Sciences, 2019, 116(20): 9999-10008). Foxp3-Treg cells are a class of immunosuppressive cells, and the excessive proliferation of Foxp3$^+$Treg cells will inhibit ICIs action. Therefore, the inhibition of a number of Foxp3$^+$Treg cells in a tumor may prevent or treat the non-responsiveness to ICIs and the development of HPD.

Baicalin has a regulatory effect on immune cells, but the role and efficacy of baicalin for non-response and hyperprogression caused by excessive Foxp3$^+$Treg cells in treatment by ICIs has not been reported. The present disclosure is intended to investigate the non-response and hyperprogression defects caused by excessive Foxp3$^+$Treg cells in treatment by ICIs and provide a technical solution to overcome the defects through a synergistic action of baicalin.

SUMMARY

The present disclosure provides a use of baicalin in preparation of a drug for treating a tumor irresponsive to ICIs/undergoing hyperprogression caused by excessive Foxp3$^+$Treg cells in view of the non-response and hyperprogression defects caused by excessive Foxp3$^+$Treg cells in treatment by ICIs. The drug can effectively overcome the above treatment defects of non-response/hyperprogression.

To achieve the above objective, the present disclosure adopts the following technical solutions:

The present disclosure provides a use of baicalin in preparation of a drug for treating a tumor irresponsive to ICIs/undergoing hyperprogression caused by excessive Foxp3$^+$Treg cells.

In the use of baicalin, the tumor irresponsive to ICI/undergoing hyperprogression caused by excessive Foxp3$^+$Treg cells is at least one selected from the group consisting of melanoma, non-small cell lung cancer (NSCLC), renal cell carcinoma (RCC), liver cancer, colorectal cancer (CRC), urothelial bladder cancer, and pancreatic cancer.

In the use of baicalin, the ICIs is one or a mixture of two or more selected from the group consisting of a PD-1 inhibitor, a PD-L1 inhibitor, and a CTLA-4 inhibitor.

In the use of baicalin, a mass percentage content of the baicalin in the drug is 0.05% to 99.5%; the drug is administered at a dose of 4 mg/d to 1,500 mg/d; and the drug is administered orally or enterally.

In order to facilitate the preparation of the drug, a pharmaceutically acceptable adjuvant may be used as an additive in the drug, and the drug may be prepared into a solid formulation or a liquid formulation.

The drug may usually be administered before or simultaneously with the ICIs.

When used in combination with ICIs, the baicalin in the present disclosure can inhibit a number of Foxp3$^+$Treg cells in a tumor to play an anti-tumor sensitization effect. The baicalin in the present disclosure can be used in combination with ICIs to effectively treat tumor-bearing mice irresponsive to ICIs/undergoing hyperprogression caused by excessive Foxp3$^+$Treg cells, which has no obvious adverse reactions, high safety, and promising prospects.

BRIEF DESCRIPTION OF THE DRAWINGS

In FIG. 1 to FIG. 5,

Figure 1:
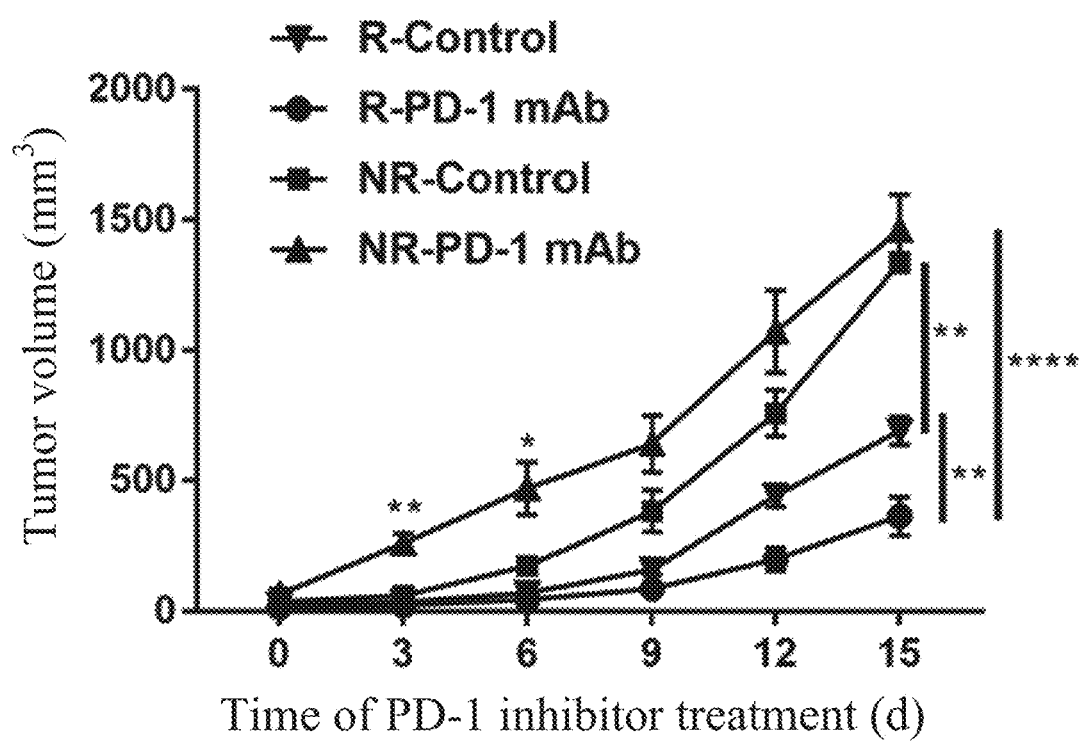
FIG. 1 shows tumor volumes of R-FMT and NR-FMT mice before and after PD-1 mAb intervention.

HQG and PD-1 mAb represent HQG and a PD-1 inhibitor, respectively;

an R-Control group and an NR-Control group represent a blank group of a response model and a blank group of a non-response/hyperprogression model, respectively;

an R-PD-1 mAb group and an NR-PD-1 mAb group represent a PD-1 inhibitor administration group of a response model and a PD-1 inhibitor administration group of a non-response/hyperprogression model, respectively;

an NR-HQG group and an NR-HQG+PD-1 mAb group represent an HQG administration group and an HQG+

PD-1 inhibitor combined administration group of a non-response/hyperprogression model, respectively; P<0.05, P<0.01, *P<0.001, and ****P<0.0001 indicate that a difference between two groups is statistically significant; and ns indicates that a difference between two groups is not statistically significant.

DETAILED DESCRIPTION OF THE EMBODIMENTS

In order to clearly elaborate an effect and action of HQG of the present disclosure, a tumor-bearing mouse model that does not respond to ICIs and undergoes hyperprogression is taken by the applicants as a research object, ICIs therapy, an HQG therapy, and an HQG+ICIs combined therapy (HQG and ICIs are simultaneously administered; or HQG is first administered and then ICIs is administered) are applied to the model, and then changes in the tumor volume and tumor weight in mice are investigated. Results show that a tumor volume of the single ICIs therapy group is significantly larger than a tumor volume of the control group on day 3 and day 6 of administration, indicating the occurrence of hyperprogression; from day 9 to the end of the experiment, a tumor volume tends to increase compared with the control group, but there is no significant difference, starting from day 12, a tumor volume of mice in the HQG+ICIs combined therapy group tends to decrease compared with the control group, and there is a significant difference in the decrease on day 15; and there is no significant difference between the single HQG therapy group and the control group in terms of the tumor volume and weight. The results show that the HQG+ICIs combined therapy can improve the non-response to ICIs and hyperprogression of tumor-bearing mice, but the single HQG therapy is ineffective.

With the solution of the present disclosure, the applicants also investigate a number of Foxp3$^+$Treg cells in the above-mentioned tumor-bearing mouse model, and results show that a number of Foxp3$^+$Treg cells in a tumor-bearing mouse control group that does not respond to ICIs is increased compared with a tumor-bearing mouse control group that responds to ICIs, indicating that the non-response to ICIs and hyperprogression may be related to an immunosuppressive effect produced due to an increase of Foxp3$^+$Treg cells in a tumor. In addition, a number of Foxp3$^+$Treg cells in a tumor is not reduced after the single HQG therapy, but a number of Foxp3$^+$Treg cells is significantly reduced after the HQG+ICIs combined therapy, indicating that the HQG+ICIs combined therapy can reduce a number of Foxp3$^+$Treg cells in a tumor to promote an immunomodulatory effect of the ICIs and improve the non-response to ICIs and hyperprogression of tumor-bearing mice.

In the above research, there are no significant adverse reactions in the single HQG therapy group and the HQG+ICIs combined therapy group.

In order to verify an accuracy of the above results, results and data in a specific experimental process are introduced and analyzed below. In order to clearly and definitely introduce the drugs and reagents used in an experimental test, names, item numbers, and manufacturer information of different reagents are listed in Table 1.

TABLE 1

Main materials and sources adopted in the examples of the present disclosure

| No. | Reagent | Item No./CAS | Company |
|---|---|---|---|
| 1 | Micropipette | — | Eppendorf |
| 2 | Ice maker | — | SANYO |
| 3 | Low-speed horizontal centrifuge | — | Anhui USTC Zonkia Scientific Instruments Co., Ltd. |
| 4 | Flow cytometer CytoFlex S | — | Beckman |
| 5 | HQG | 21967-41-9 | Baoji Herbest Bio-Tech Co., Ltd. |
| 6 | Ampicillin | 69-53-4 | Shanghai Topscience Co., Ltd. |
| 7 | Metronidazole | 443-48-1 | Shanghai Topscience Co., Ltd. |
| 8 | Neomycin sulfate | 1405-10-3 | Shanghai Topscience Co., Ltd. |
| 9 | Vancomycin | 1404-93-9 | Shanghai Topscience Co., Ltd. |
| 10 | Medium (DMEM-H) | SH30243.01 | Hyclone |
| 11 | Fetal bovine serum (FBS) | 11011-8611 | Zhejiang Tianhang Biotechnology Co., Ltd. |
| 12 | Mouse lymphocyte separation medium | 7211011 | Biolegend |
| 13 | Trypsin-EDTA 0.25% | SH30042.01B | Hyclone |
| 14 | PBS | SH30256.01 | Hyclone |
| 15 | Lewis lung cancer | — | Peking Union Cell Resource Center |
| 16 | InVivoPlus anti-mouse PD-1(CD279) | 810421D1 | Bio X Cell |
| 17 | PE/Cyanine7 anti-mouse CD4 | 116016 | Biolegend |
| 18 | Brilliant Violet 510 ™ anti-mouse CD25 | 102041 | Biolegend |
| 19 | Alexa Fluor ® 700 anti-mouse FOXP3 | 126421 | Biolegend |
| 20 | Cell Activation Cocktail (with Brefeldin A) | 423303 | Biolegend |
| 21 | True-Nuclear ™ Transcription Factor Buffer Set | 424401 | Biolegend |

Example 1 Preparation of Experimental Solutions

Preparation of broad-spectrum antibiotics (ABT): An appropriate amount of each of neomycin sulfate, metronidazole, ampicillin, and vancomycin was weighed, and normal saline (NS) was added to obtain a 40 mg/mL neomycin sulfate solution, a 40 mg/mL metronidazole solution, a 40 mg/mL ampicillin solution, and a 20 mg/mL vancomycin solution; and the solutions were thoroughly mixed, and a resulting mixed solution was dispensed into 15 mL centrifuge tubes and stored at −20° C. for later use.

Preparation of fecal suspensions for clinical patients: Pre-frozen fecal samples of clinical PD-1 mAb-responsive patients (R) and PD-1 mAb-irresponsive patients (NR) with NSCLC each were suspended in a sterile sodium chloride solution (0.9%) with 1 g of feces per 10 mL, and resulting mixtures each were thoroughly stirred until there were no obvious large particles; the mixtures each were filtered through a 200-mesh sterile mesh sieve to remove large particles in feces, and resulting filtrates each were collected in a sterile centrifuge tube and vortexed for 5 min to obtain suspensions; and the suspensions each were centrifuged at 600×g for 5 min to remove insoluble matters, and resulting supernatants each were immediately dispensed in a clean bench and then stored at −20° C. for later use.

Preparation of an HQG solution for intragastric administration: An appropriate amount of HQG was weighed and prepared with NS into a 20 mg/mL suspension, and the suspension was stored at −20° C. for later use.

Preparation of a PD-1 mAb solution: An appropriate amount of PD-1 mAb was taken and prepared with NS into a 2.5 mg/mL suspension, which was prepared just before use.

Example 2 Establishment of a PD-1 mAb-Irresponsive Lewis Lung Carcinoma (LLC)-Bearing Mouse Model Pseudo-germ-free mouse modeling: Mice were treated with broad-spectrum antibiotics to construct pseudo-germ-free mouse models. 36 female C57BL/6J mice at 5 weeks (experimental animal license No.: SCXK (Beijing) 2019-0009) were purchased from Beijing Vital River Laboratory Animal Technology Co., Ltd. The mice were raised under the following conditions: cleanliness: SPF level; room temperature: 20° C. to 22° C.; humidity: 60±5%; 12 h light/12 h dark alternating cycle; and free eating and drinking. All animal protocols in this experiment were approved by the Beijing MaideiKangna Animal Ethics Committee, and animal experimental operations were conducted under the guidance of the Laboratory Animal Protection Association.

After the mice were raised adaptively for one week, the mice were intragastrically administered daily with 100 μL of ABT for consecutive 3 days.

LLC-Bearing Mouse Modeling Through Transplantation of Fecal Bacteria:

Transplantation of fecal bacteria: 2 d after the administration of ABT was stopped, frozen fecal suspensions (1 g/10 mL) of clinical PD-1 mAb-responsive patients (R) and PD-1 mAb-irresponsive patients (NR) with NSCLC were taken out, heated in a water bath at 37° C., and intragastrically administered to ABT-treated mice, where each mouse was intragastrically administered with 100 μL of the suspension for consecutive 7 days.

Subcutaneous inoculation of LLC cells: An LLC cell suspension with a concentration of about $1 \times 10^7$ cells/mL was inoculated at a right axilla of a fecal bacteria-transplanted mouse with an inoculum size of 0.2 mL/mouse. The longest and shortest diameters of a tumor were measured by a vernier caliper, and a volume of the tumor=½ longest diameter×shortest diameter$^2$.

R-FMT refers to PD-1 mAb-responsive LLC-bearing mice transplanted with fecal bacteria; and NR-FMT refers to PD-1 mAb-irresponsive LLC-bearing mice transplanted with fecal bacteria.

Example 3 Therapeutic Effect of HQG for PD-1 mAb-Irresponsive LLC-Bearing Mice

When mouse tumors grew to 20 mm$^3$ to 50 mm$^3$, mice of an R-FMT group were divided into an R-Control group and an R-PD-1 mAb group, and mice of the NR-FMT group were divided into an NR-Control group, an NR-PD-1 mAb group, an NR-HQG group, and an NR-HQG+PD-1 mAb group, with 6 mice in each group. Administration modes and doses were as follows:

R-Control and NR-Control groups: Mice were intragastrically administered with NS daily until the end of the experiment (200 μL/d); and the mice were intraperitoneally injected with NS (100 μL/time) once every 3 days, with 5 injections in total.

R-PD-1 mAb and NR-PD-1 mAb groups: Mice were intragastrically administered with NS daily until the end of the experiment (200 μL/d); and the mice were intraperitoneally injected with PD-1 mAb (100 μL/time) once every 3 days, with 5 injections in total.

NR-HQG group: Mice were intragastrically administered with HQG daily until the end of the experiment (200 μL/d); and the mice were intraperitoneally injected with NS (100 μL/time) once every 3 days, with 5 injections in total.

NR-HQG+PD-1 mAb group: Mice were intragastrically administered with HQG daily until the end of the experiment (200 μL/d); and the mice were intraperitoneally injected with PD-1 mAb (100 μL/time) once every 3 days, with 5 injections in total.

During administration, a body weight of mice was monitored every 3 days, and a tumor volume was measured.

Figure 2:
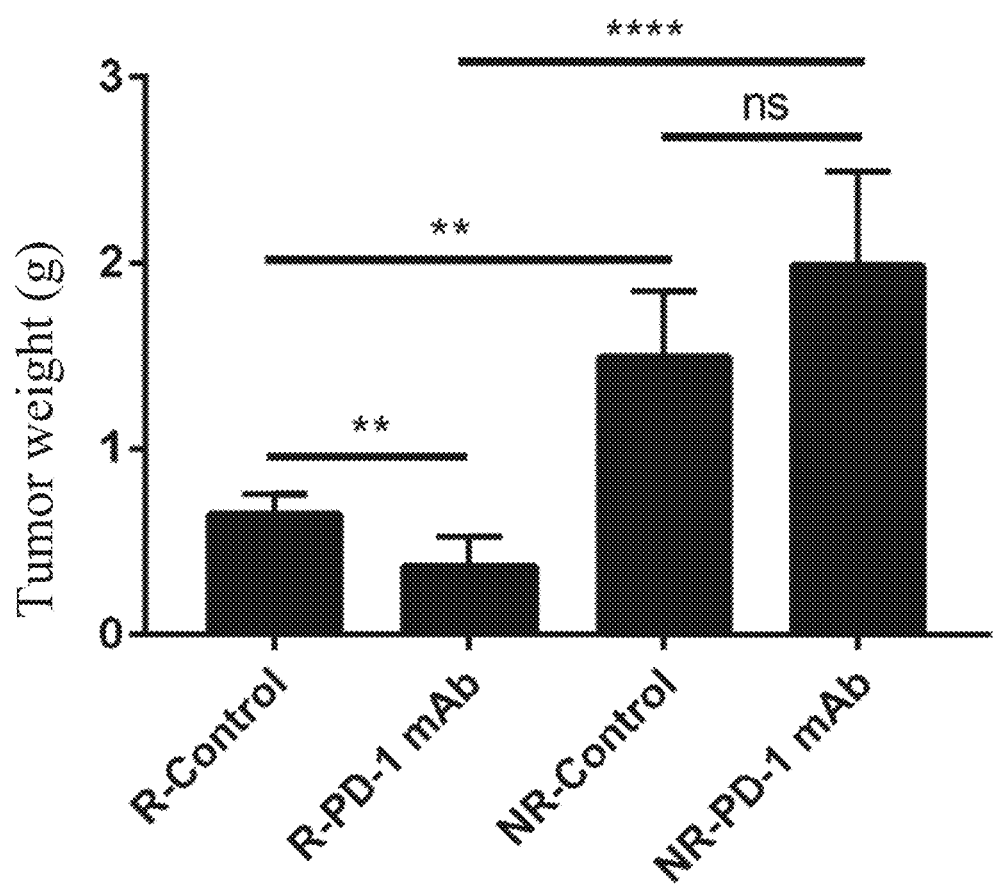
FIG. 2 shows tumor weights of R-FMT and NR-FMT mice before and after PD-1 mAb intervention.

Results are shown in FIG. 1 and FIG. 2. After NR-FMT and R-FMT treatments, a tumor volume and a tumor weight of tumor-bearing mice in the NR-Control group are greater than a tumor volume and a tumor weight of tumor-bearing mice in the R-Control group; after PD-1 mAb intervention, a tumor volume and a tumor weight of the R-PD-1 mAb group are reduced compared with the R-Control group, indicating that mice have an immune response; and a tumor volume and a tumor size of mice in the NR-PD-1 group are significantly larger than a tumor volume and a tumor size of mice in the NR-Control group, indicating that, after tumor-bearing mice in the NR-FMT group are intervened with PD-1 mAb, no response and hyperprogression occurs.

Figure 3:
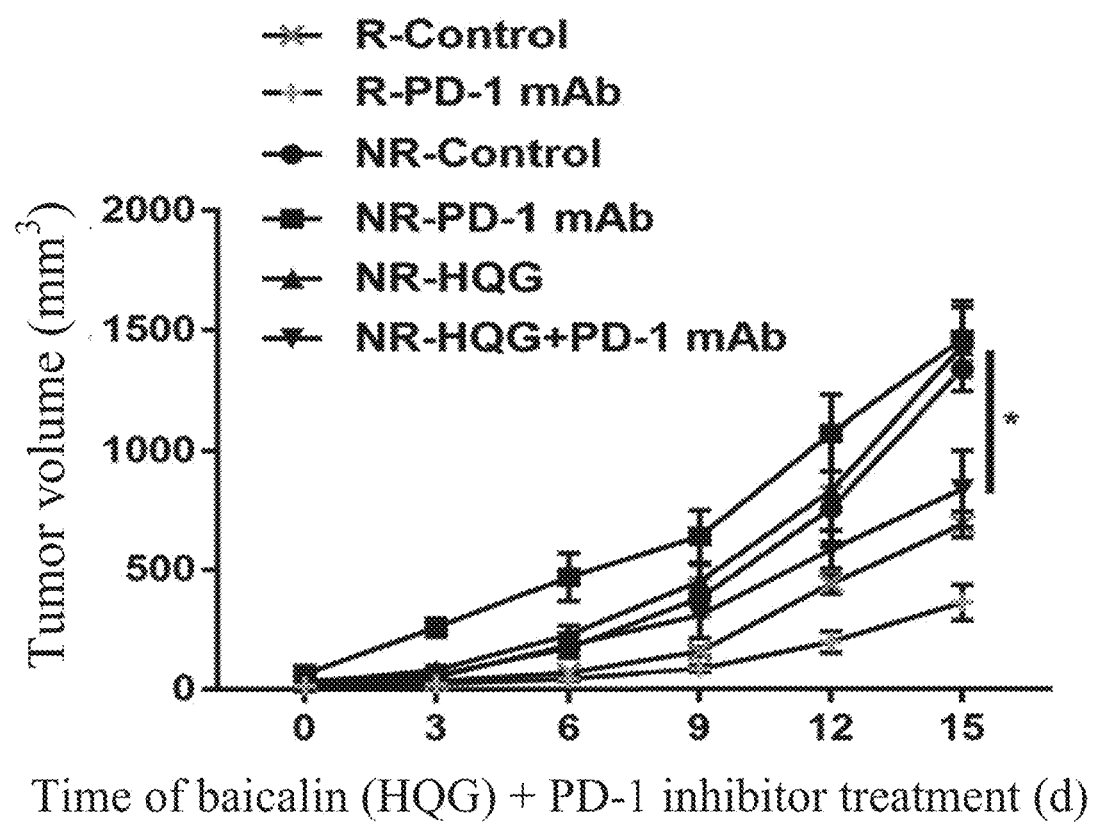
FIG. 3 shows tumor volumes of NR-FMT mice before and after PD-1 mAb intervention, baicalin (HQG) intervention, and HQG+PD-1 mAb intervention.
Figure 4:
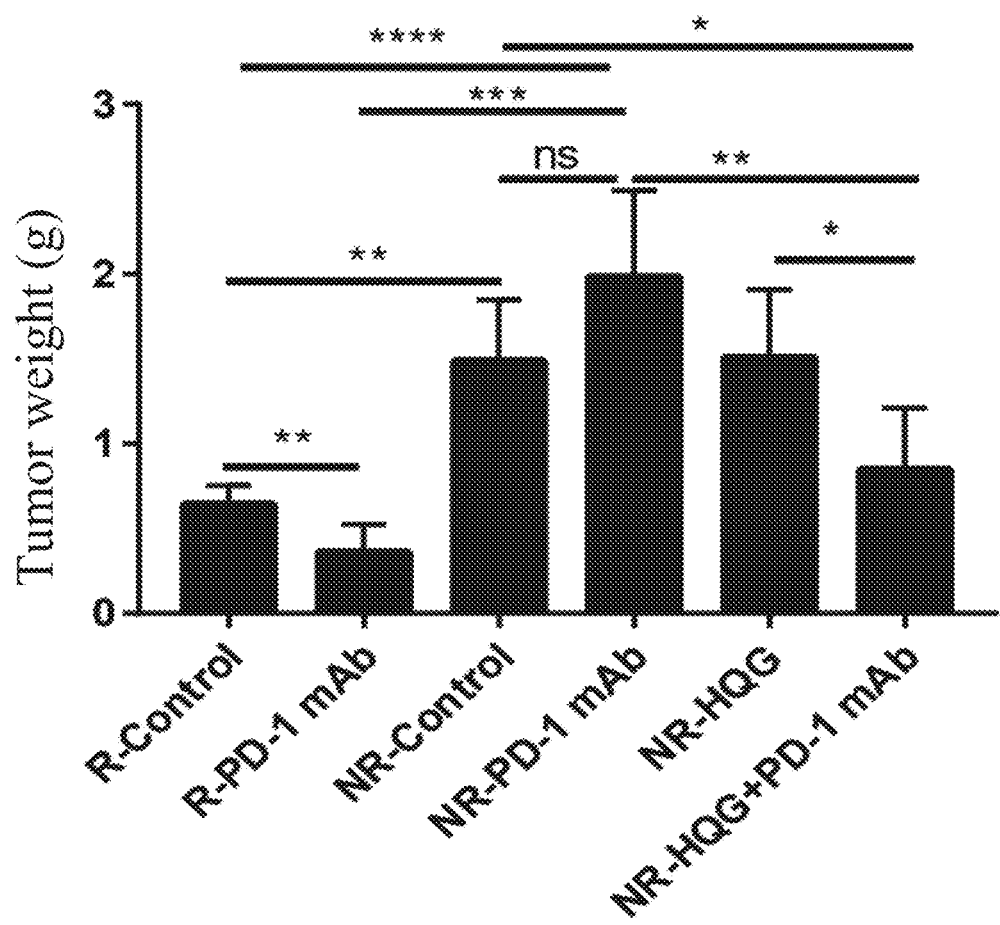
FIG. 4 shows tumor weights of NR-FMT mice before and after PD-1 mAb intervention, HQG intervention, and HQG+PD-1 mAb intervention.

Compared with the NR-Control group, a tumor volume and a tumor weight of mice are not reduced after the therapy in the NR-HQG group, but the NR-HQG+PD-1 mAb group can significantly reduce the tumor volume and weight increases caused by non-response to NR-PD-1 mAb and hyperprogression, as shown in FIG. 3 and FIG. 4.

Example 4 Detection of Foxp3$^+$Treg Cells in a Tumor Tissue by FCM 0.2 mL of fresh ethylenediaminetetraacetic acid (EDTA) anticoagulant blood was collected from 5 mice in each of the R-Control group, R-PD-1 mAb group, NR-Control group, NR-PD-1 mAb group, NR-HQG group, and NR-HQG+PD-1 mAb group, and mixed with phosphate-buffered saline (PBS) at 1:1; a clean centrifuge tube was taken, 1 mL of a mouse lymphocyte separation medium was added, and a blood-PBS mixture was slowly added to a liquid level of the 1 mL of the mouse lymphocyte separation medium; and the centrifuge tube was centrifuged at 800 g for 30 min with an ascending speed 7 and a descending speed 3, and a resulting intermediate lymphocyte layer was collected. A tumor tissue was added to 3 mL of PBS and gently ground, a resulting mixture was then filtered through a 200-mesh filter mesh, and a resulting filtrate was collected into a centrifuge tube; a clean centrifuge tube was taken, 3 mL of a mouse lymphocyte separation medium was added, and 2 mL of the tumor single-cell suspension was slowly added to a liquid level of the 3 mL of the mouse lymphocyte separation medium; a resulting mixture was centrifuged at 800 g for 30 min with an ascending speed 7 and a descending speed 3, and a resulting intermediate lymphocyte layer was collected, and 2 mL of PBS was added to wash the cells, a resulting suspension was centrifuged at 500 g for 5 min, and a resulting supernatant was discarded (if there were obvious red blood cells (RBCs), 2 mL of an RBC lysis buffer was added to wash the cells, a resulting suspension was centrifuged at 500 g for 5 min, and a resulting supernatant was discarded; and then the cells were washed with 2 mL of PBS). The cells were resuspended with an RPMI 1640 complete medium, and $2\times10^6$ cells were transferred to a pointed-bottom 96-well plate; 0.2 μL of Cell Activation Cocktail (with Brefeldin A) (1:1,000) was added to each well, and the plate was incubated at 37° C. and 5% $CO_2$ for 5 h; after the incubation was completed, a resulting system was centrifuged, and a resulting supernatant was discarded; 1 μL of each of antibodies CD4 and CD25 was added, and the plate was incubated at room temperature in the dark for 15 min; 0.2 mL of a cell fixation solution was added to fix at room temperature in the dark for 30 min, a resulting system was centrifuged at 500 g for 5 min, and a resulting supernatant was discarded; 0.2 mL of a 1× cell disruption solution was added, a resulting system was centrifuged, and a resulting supernatant was discarded; 0.2 mL of a 1× cell disruption solution was added once again, a resulting system was centrifuged, and a resulting supernatant was discarded; 1 μL of a Foxp3 antibody was added, and a resulting mixture was incubated at room temperature in the dark; 0.2 mL of a cell disruption solution was added, a resulting system was centrifuged, and a resulting supernatant was discarded; and the cells were resuspended with 0.1 mL of a cell staining buffer, and a resulting cell suspension was tested on a machine.

Figure 5:
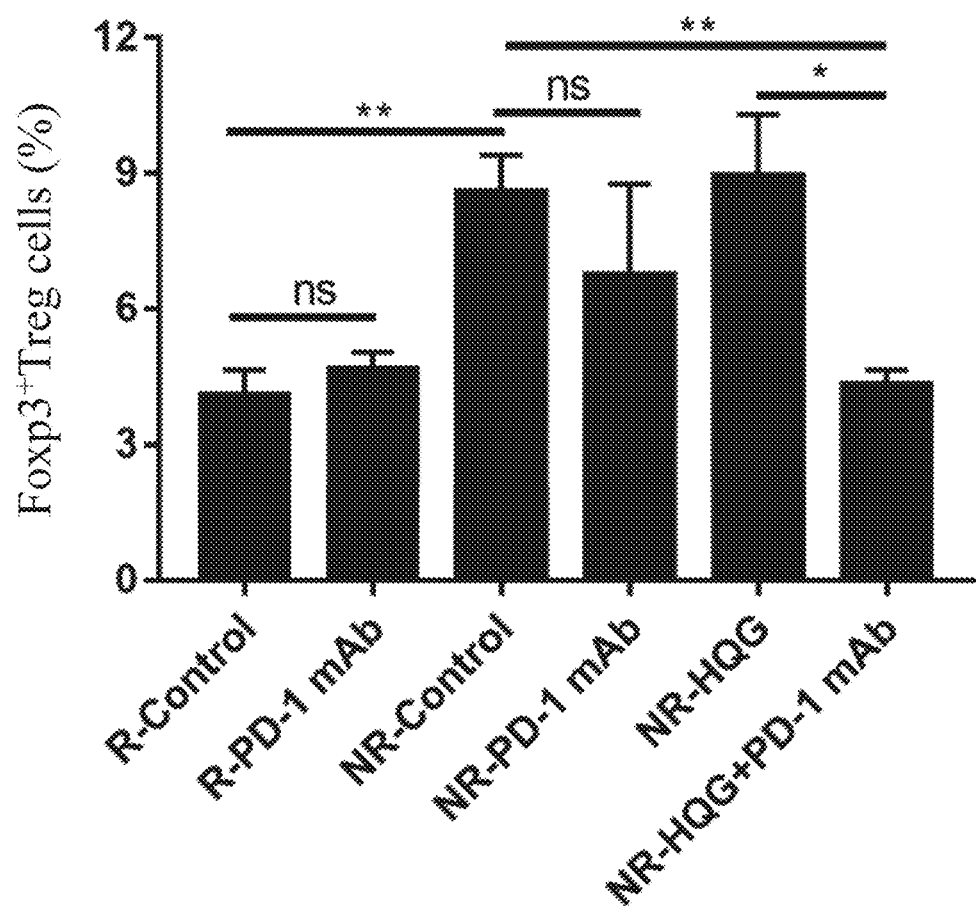
FIG. 5 shows numbers of intratumor Foxp3$^+$Treg cells in NR-FMT mice before and after PD-1 mAb intervention, HQG intervention, and HQG+PD-1 mAb intervention.

Results are shown in FIG. 5. Compared with the R-Control group, a number of Foxp3-Treg cells in the NR-Control group is significantly increased; and before and after PD-1 mAb intervention, there is no significant difference in a number of Foxp3$^+$Treg cells between the two groups, indicating that the hyperprogression of a tumor may be related to an immunosuppressive effect caused by an increase of Foxp3$^+$Treg cells in the tumor. In addition, a number of Foxp3$^+$Treg cells in a tumor is not reduced after the single HQG therapy, but a number of Foxp3$^+$Treg cells is significantly reduced in the HQG+PD-1 mAb combined therapy group, indicating that the HQG+PD-1 mAb combined therapy can reduce a number of Foxp3-Treg cells in a tumor and an immunosuppressive effect caused accordingly, thereby promoting an immunomodulatory effect of PD-1 mAb.

The specific examples of the present disclosure are merely intended to explain the present disclosure, and do not limit the present disclosure. Those skilled in the art can make modifications without creative efforts to the examples as needed after reading this specification, but these modifications are protected by the patent law as long as they fall within the scope defined by the claims of the present disclosure.

What is claimed is:

1. A method of treating a tumor irresponsive to PD-1 immune checkpoint inhibitors (ICIs) and undergoing hyperprogression, wherein the tumor is non-small cell lung cancer and a non-response to the PD-1 ICIs and hyperprogression of the tumor is caused by excessive Foxp3$^+$Treg cells, comprising:
   detecting the presence of Foxp3$^+$Treg cells in a non-small cell lung cancer tumor tissue as an indication of hyperprogression, wherein a Foxp3 antibody is used for detecting the presence of Foxp3$^+$Treg cells;
   preparing a drug by adding baicalin to a pharmaceutically acceptable adjuvant, wherein a mass percentage content of the baicalin in the drug is 0.05% to 99.5%; and
   administering the drug orally or enterally in combination before or simultaneously with a PD-1 ICI monoclonal antibody, wherein the drug is administered at a dose of 4 mg/d to 1,500 mg/d until a number of Foxp3$^+$Treg cells in the tumor tissue is reduced.

2. The method of treating a tumor irresponsive to PD-1 ICIs and undergoing hyperprogression according to claim 1, wherein a formulation for the drug is a solid formulation or a liquid formulation.

* * * * *